(12) United States Patent
Ginggen

(10) Patent No.: US 6,926,246 B2
(45) Date of Patent: Aug. 9, 2005

(54) METHOD OF SETTING AND ACTUATING A MULTI-STABLE MICRO VALVE AND ADJUSTABLE MICRO VALVE

(75) Inventor: Alec Ginggen, Muntschemier (CH)

(73) Assignee: Medos S.A. (CH)

( * ) Notice: Subject to any disclaimer, the term of this patent is extended or adjusted under 35 U.S.C. 154(b) by 157 days.

(21) Appl. No.: 10/263,504

(22) Filed: Oct. 3, 2002

(65) Prior Publication Data

US 2003/0155539 A1 Aug. 21, 2003

(51) Int. Cl.⁷ .................................................. F15C 5/00
(52) U.S. Cl. ....................................................... 251/11
(58) Field of Search ............................................ 251/11

(56) References Cited

U.S. PATENT DOCUMENTS

| 5,619,177 A | 4/1997 | Johnson et al. |
| 5,697,951 A | 12/1997 | Harpstead et al. |
| 6,149,123 A | 11/2000 | Harris et al. |

6,354,839 B1 * 3/2002 Schmidt et al. ............. 434/113

FOREIGN PATENT DOCUMENTS

| DE | 196 45725 | 12/1997 |
| EP | 0778 043 A | 6/1997 |
| WO | WO 99/38551 A | 8/1999 |
| WO | WO 99/39118 A | 8/1999 |

* cited by examiner

Primary Examiner—J. Casimer Jacyna

(57) ABSTRACT

A micro valve and a method for setting or actuating a micro valve for use in fluidic applications includes cooling an array of actuating members made of Shape Memory Alloy (SMA) material. The SMA material is cooled to a temperature equal to or below the temperature at which a transformation from austenitic to martensitic state occurs so that the entire array of SMA actuating members is either fully or partially in the martensitic state. At least one of the actuating member is selected to correspond to a pre-determined opening pressure or flow resistance. Each of the actuating members are heated individually, except the previously selected one, to a temperature equal to or above the temperature at which a transformation from the martensitic state to the austenitic state occurs.

4 Claims, 5 Drawing Sheets

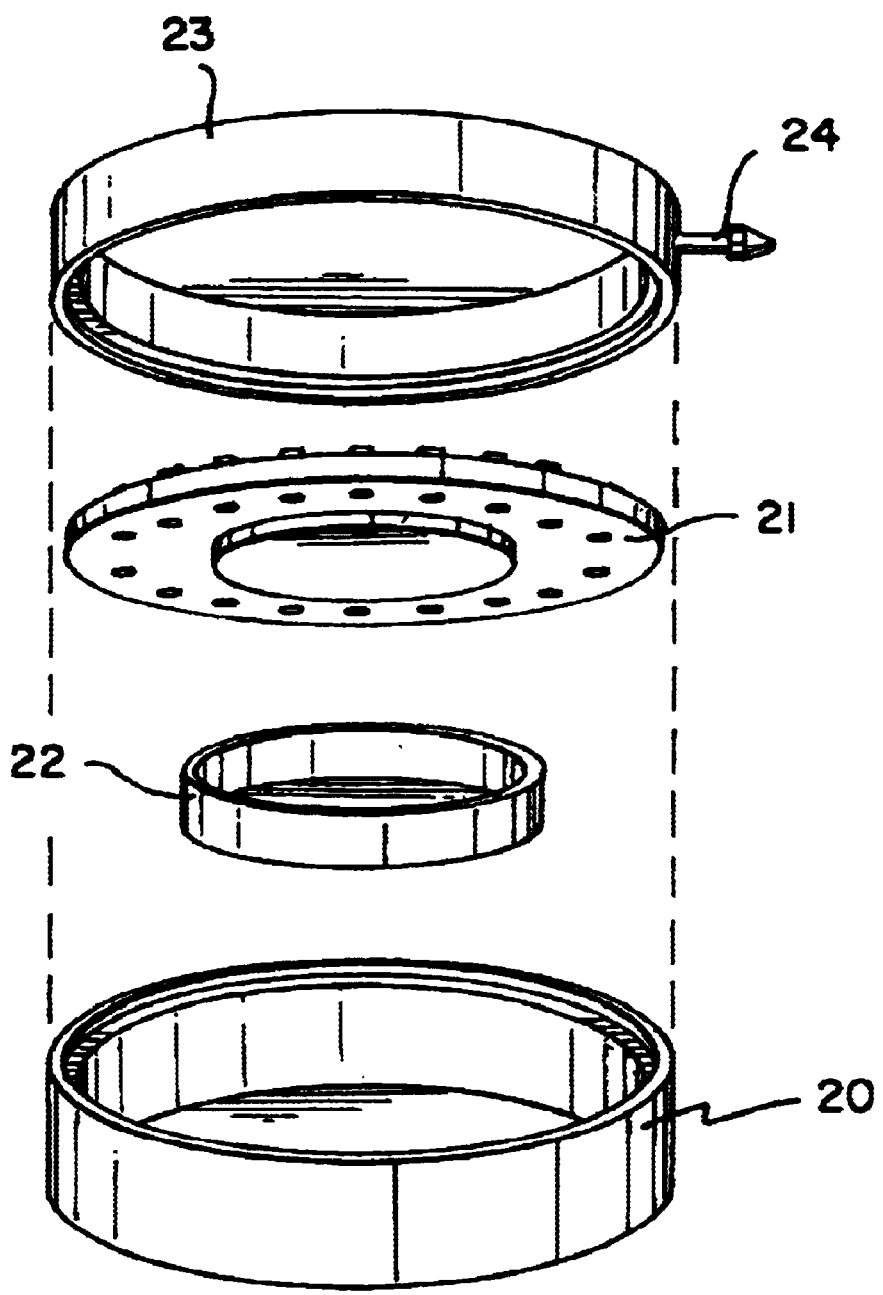

METHOD OF SETTING AND ACTUATING A MULTI-STABLE MICRO VALVE AND ADJUSTABLE MICRO VALVE

BACKGROUND OF THE INVENTION

1. Field of the Invention

The present invention relates to a method of setting and/or actuating a multi-stable valve used in fluidic or in micro fluidic applications. Another object of the invention is an adjustable multi stable valve for use in medical devices implanted in a human body.

More specifically, the invention relates to a micro valve having at least two stable states at operating temperature. An opening pressure and a resistance to fluid flow correspond to each state of the valve. The valve may be actuated non-invasively, by telemetry for example, with an external device, providing an adjustable opening pressure valve or alternatively a valve assembly with adjustable resistance to flow.

2. Discussion of the Related Art

The valve object of the present invention has a wide range of applications in different fields (medical, hydraulics, micro-engineering, etc.). For example, in the medical field related to the treatment of hydrocephalic patients, it is necessary to install a shunt system that derives the excess of liquid from the brain to the peritonea or to another cavity of the patient. Some existing shunt systems comprise an adjustable valve that allows the surgeon to modify non-invasively the valve opening pressure after implantation. These existing implantable valves for the treatment of hydrocephalic patients have successfully shown that the feature allowing the surgeon to adjust non-invasively the valve opening pressure after implantation is extremely useful. Nevertheless, there are some drawbacks associated with devices of this type that can be summarized as follows:

These known implants do not provide the user with any feedback during or after adjustment of the valve opening pressure. Therefore, it might be necessary to take an X-ray for checking the valve setting. Furthermore, the valve can be misadjusted by strong magnetic fields, such as those generated by a permanent magnet found for example in magnetic resonance imaging devices.

Finally the existing valves are sometimes blocked due to an accumulation of bio-substance on the mechanical parts of the valve mechanism.

Some other known electromechanical or pneumatic valves require energy for remaining in one or more working positions and are not suitable for human or animal implantation due to their size and/or their lack of tightness.

SUMMARY OF THE INVENTION

The valve object of the present invention overcomes the problems exposed above by providing a micro valve having at least two stable states at operating temperature. The valve according to the invention does not require energy at rest during normal operation and is insensitive to magnetic fields by design. Since the valve setting may be adjusted without mechanical movement of any parts, the valve is less sensitive to blockage due to an accumulation of bio substances.

The actuation concept is based on temperature changes above and below body temperature. Energy is only required to change the valve from one state to the other. Valves for the treatment of hydrocephalic patients, as well as valves for all kind of implantable pumps constitute major applications of that concept that may be extended to other fields.

These and other drawbacks are overcome with a method in accordance with the present invention for setting and actuating an implantable valve having the steps of cooling an array of actuating members made of SMA material to a temperature equal or below the temperature at which a transformation from austenitic to martensitic state occurs so that the entire array of SMA actuating members is either fully or partially in the martensitic state. At least one of the actuating members corresponding to a pre-determined opening pressure or resistance to flow is selected. Each of the actuating members, except the previously selected members are individually heated to a temperature equal to or above the temperature at which a transformation from the martensitic state to the austensitic state occurs.

These and other drawbacks are also overcome with a micro valve having a base element with at least one passage for the flow of fluid. At least one array of actuating members is made of a SMA material is arranged on the base plate face. The at least one array of actuating members has a device for cooling one or all of the actuating members. The at least one array of actuating members has a device for heating one or all of the actuating members.

BRIEF DESCRIPTION OF THE DRAWINGS AND FIGURES

Further features and other objects and advantages of this invention will become clear from the following detailed description made with reference to the accompanying drawings illustrating in a schematic and non-limiting way three embodiments of a multi stable micro valve according to the invention and in which:

FIG. 14 is an exploded perspective view of an implantable pump embodying a valve according to the invention.

DETAILED DESCRIPTION OF THE PRESENT INVENTION

In the following disclosure, reference will be made to shape memory alloys, hereafter called SMA material. The properties and characteristics of such materials are briefly described in the following.

SMA material is characterized by reversible metallurgical phase transformations that are activated either by temperature change or by induced stress. Below a range of transition temperature, the material is in the martensitic state, whereas above that temperature range, the material is in the austenitic state. The transformation occurs across a range of temperatures which are commonly named $A_s$ (start) and $A_f$ (finish) for the transformation from martensitic to austenitic state and $M_s$ (start) and $M_f$ (finish) for the transformation from austenitic to martensitic state as referenced in FIG. 1. These transformations are reversible so that the material may be treated to assume different shapes in each of the two phases, and can reversibly switch between the two shapes when transformed from one state to the other. More commonly, the material is treated to only return to a shape upon transformation to the austenitic phase a biasing force, acting against the SMA material returns it to its alternate shape upon transformation to the martensitic phase.

Figure 1:
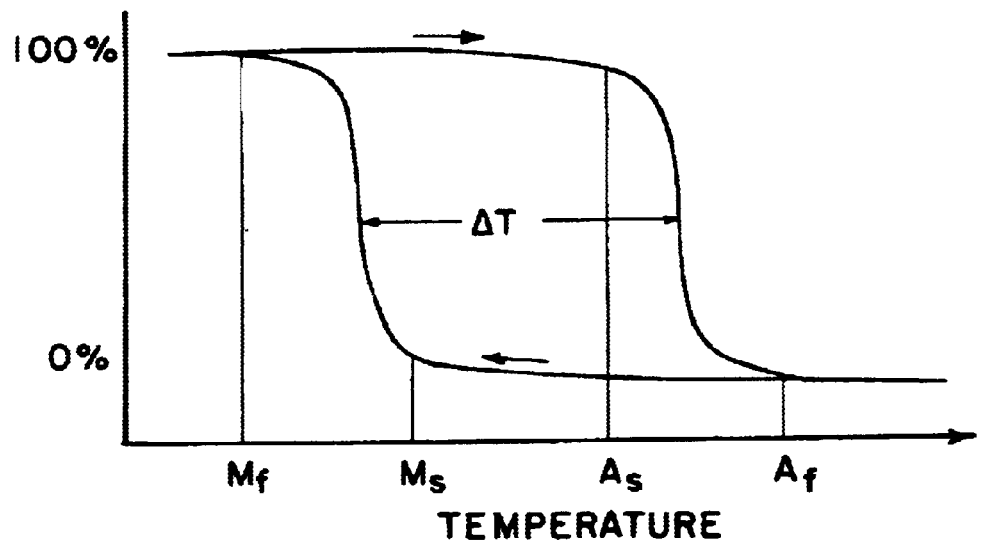
FIG. 1 is a graph showing the typical temperature hysteresis of shape memory alloy (SMA).

Most of the temperature cycles of the SMA materials have a hysteresis $\Delta T$, as illustrated on the graph of FIG. 1.

Figure 2:
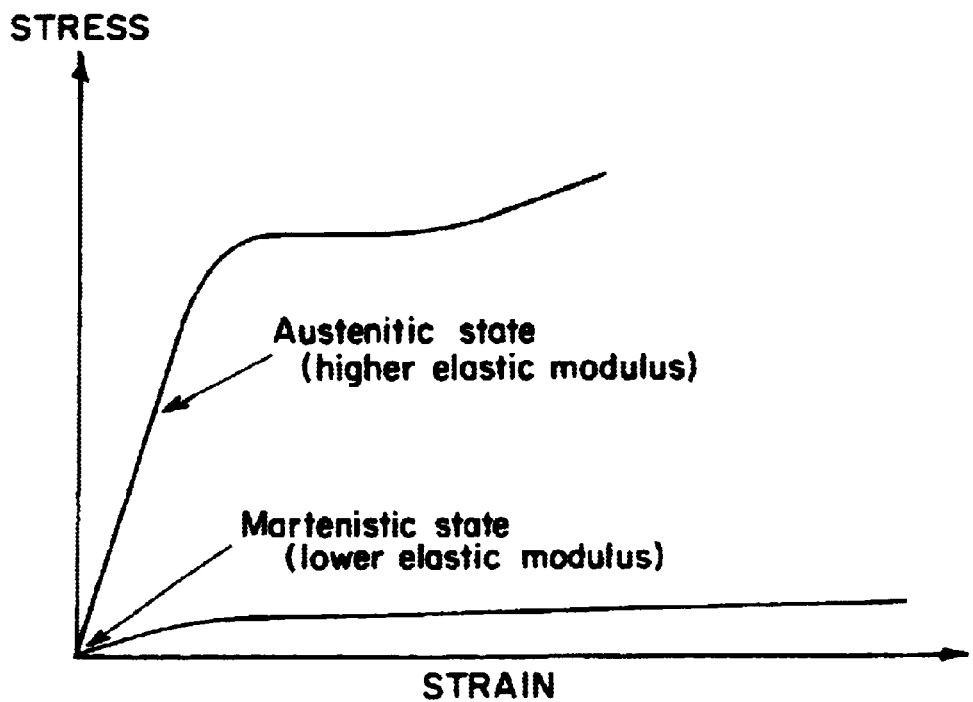
FIG. 2 is a graph showing the typical stress-strain characteristics of a shape memory alloy in each of its states.

The elastic modulus of the SMA material depends on its metallurgical state. FIG. 2 shows a typical stress-strain graph of a SMA material in both states. It appears clearly that the austenitic state has a higher elastic modulus than the martensitic state. Upon initial loading, the stress-strain curve is roughly linear and the Young's modulus corresponds to the slope of the curve in the initial loading region. For materials tested at temperatures just above the $A_f$ temperature, if the material is further deformed beyond this initial loading region, it will experience a stress-induced martensitic transformation. The point on the stress-strain curve at which the stress-induced martensitic, transformation begins can be called the $M_s^\circ$.

In the martensitic state, the elastic modulus is lower than in the austenitic state, and the corresponding $M_s^\circ$ (in this case, the stress required to rearrange the pre-existing martensitic phase) is also lower.

The invention makes use of the change in mechanical properties (mainly Young's modulus) of an array of actuators in SMA material when a transition between the two metallurgical states occurs.

For medical implantable devices, the SMA material is preferably chosen within SMA materials having a working temperature corresponding to body temperature located between $M_s$ and $A_s$. In that case, the material is stable in both states at rest. Heating the material above $A_f$ will transform it into austenite (higher modulus material). Cooling the material below $M_f$ will transform it into martensite (lower modulus material). While the effect is most pronounced with the temperature of use located between $M_s$ and $A_s$, the effect can be observed to some extent at a number of temperatures in the broader range between $M_f$ and $A_f$.

For example TiNi (Nitinol) is a good choice for the actuating members of a valve according to the invention as it is biocompatible. Further, TiNi can be manufactured such that body temperature is located between $M_s$ and $A_s$. A TiNi material manufactured to meet this criterion might have the following characteristics: Martensitic transformation: $M_f=24°$ C. $M_s=36°$ C. Austenitic transformation: $A_s=54°$ C. $A_f=71°$ C. with a hysteresis: $\Delta T\sim35°$ C. Note that the transformation temperatures for a particular material also change with stress, so that the temperatures of the starting material must be selected to appropriately accommodate the variability due to the operating stresses of the particular application.

Fine tuning the temperature cycle and the mechanical properties may be achieved by playing with the chemical composition and thermomechanical processing of the material.

As it will be described in detail with reference to the figures, the micro valve object of the invention comprises an array of actuators or actuating members made of a SMA material that interact either directly with the fluid path or with an elastic mean, the tension of which being modified by the array of SMA actuators.

The SMA material is selected to have two stable metallurgical states at the temperature of use, e.g., body temperature. The metallurgical state can be changed either by cooling or by heating the SMA actuator. One of the metallurgical states has a higher elastic modulus, whereas the other state has a lower elastic modulus.

The heating is obtained by circulating a current through or in the proximity of the SMA material (Joule effect). The cooling is achieved with a Peltier cell or an array of Peltier cells integrated in the base plate of the valve, in the vicinity of the SMA actuators.

Figure 3:
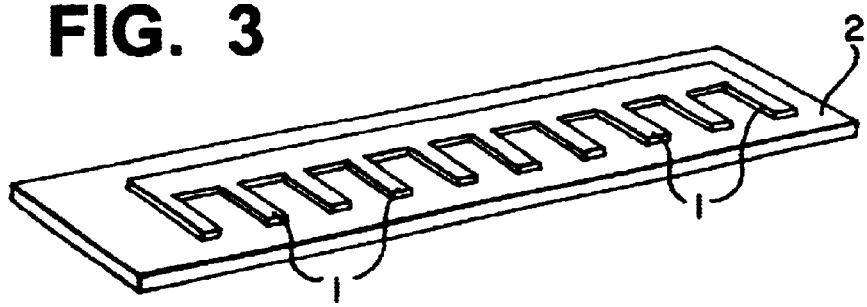
FIG. 3 is a schematic perspective top view of a first embodiment of a micro valve according to the invention.
Figure 4:
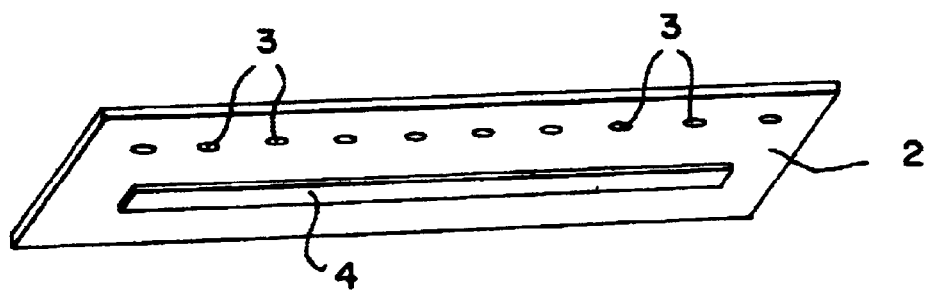
FIG. 4 is a bottom perspective view according to the first embodiment shown at FIG. 3.
Figure 5:
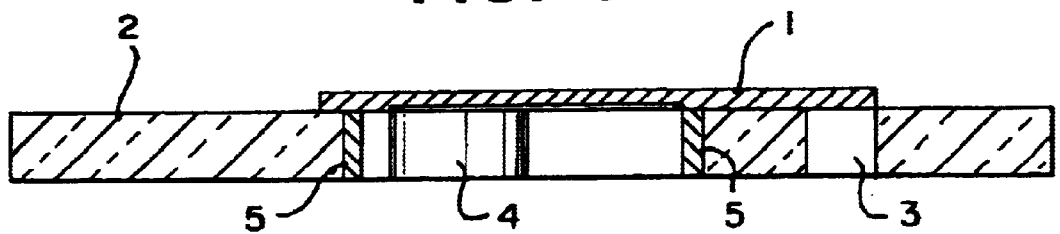
FIG. 5 is cross sectional view of the first embodiment of the valve shown at FIG. 3.

With reference to FIGS. 3,4 and 5, a first embodiment of a micro valve with adjustable opening pressure is illustrated.

The fluid path crosses a base plate 2 having an array of orifices 3, closed by the free extremity of a corresponding array of actuating members 1. The base plate 2 is preferably made of a glass type material like Pyrex for example. The geometry of the orifices 3 is identical across the array, which ensures that the resistance to fluid is the same for each single orifice 3. The array of actuating members 1 comprises, in this embodiment, an elongated body from which extend perpendicularly elongated actuating members. Some other configurations are of course possible. The actuating members 1 are made of SMA material, preferably TiNi, and their geometry is chosen so that each fluid path 3 can be considered as closed when the corresponding actuating member 1 is in the austenitic state and open in the martensitic state.

A Peltier cell 4 is integrated in the base plate 2, and allows, once energized, the cooling of the array of actuating members 1.

Each actuating member 1 may be heated individually by circulating an electrical current through the connectors 5 bounded to each of the actuating members 1.

The valve setting is modified in the following manner. First, the temperature of the array of SMA actuating members 1 is decreased to a temperature substantially lower than $M_s$ (preferably below $M_f$) by energizing the Peltier cell 4. This transforms all or part of the actuating members 1 to the martensitic state (lower modulus). Then, at least one actuating member is selected within the array and the temperature of all actuating members 1 except the previously selected is increased to a temperature substantially higher than $A_s$ (preferably above $A_f$) This is achieved by circulating an electrical current through the connectors 5 connected to the actuating members 1. Once the higher temperature is reached, all or part of the actuating members 1 are in the austenitic state (higher modulus) except the selected actuating member which remains all or partially in the martensitic state thus determining the opening pressure of the valve.

As an alternative, the array of SMA actuators may be first heated to a temperature at which an austenitic transformation occurs and then at least one selected actuating member is cooled down to a temperature at which a martensitic transformation occurs. For implementing this alternate method, an array of Peltier cells is provided. Each Peltier cell forming the array being located in the vicinity of an actuating member so as to enable the individual cooling of each actuating member.

The size and geometry of each actuating member 1 forming the array can be adjusted for providing different opening pressure depending on which actuating member remains in the martensitic state.

Figure 6:
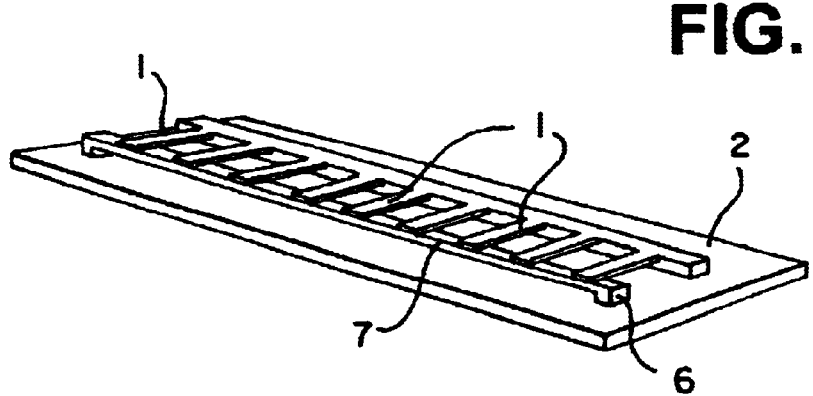
FIG. 6 is a perspective top view of a second embodiment of a micro valve according to the invention.
Figure 7:
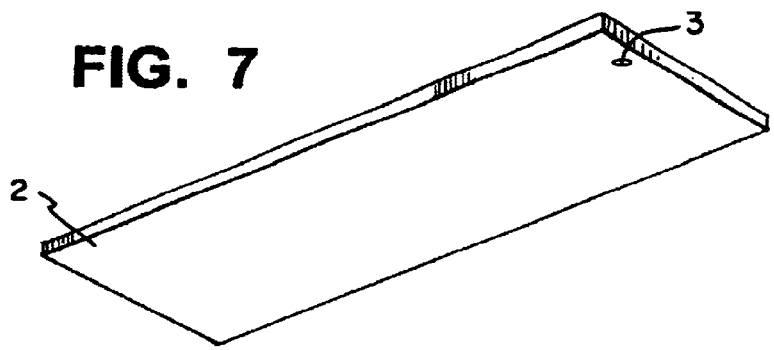
FIG. 7 is perspective bottom view of the second embodiment depicted in FIG. 6.
Figure 8:
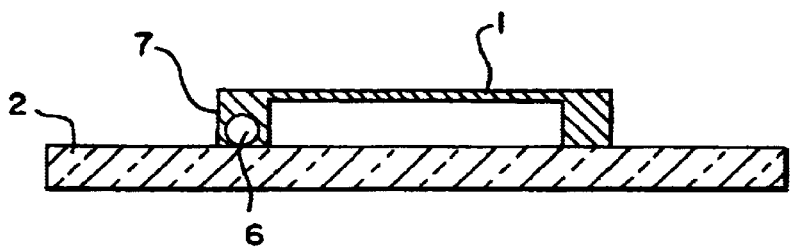
FIG. 8 is schematic cross sectional view of the second embodiment depicted in FIG. 6.

FIGS. 6, 7 and 8 depict another embodiment of a valve with an adjustable opening pressure. The base plate 2 has only one orifice 3 through which the fluid may flow. A ball 6 is maintained in the seat of the orifice 3 with an elastic element like a flexible flat spring 7 for example. The spring 7 need not be made of a SMA material.

An array of SMA actuating members 1 is arranged perpendicularly to the spring 7 and the free end of each actuating member 1 interacts with the spring 7. Depending on the metallurgical state of the SMA actuating members 1, the length of the spring allowed to move freely is restricted. The force applied to the ball is determined by the tension of the spring 7 which varies with the metallurgical states of the actuating members 1.

A Peltier cell is integrated in the base plate 2 in the vicinity of the SMA array of actuating members 1. Upon activation, the Peltier cell cools the array and all the actuating members 1 change to martensitic state. Each of the actuating members 1 may then be individually heated to a temperature at which an austenitic transformation occurs. This determines the length of activation of the spring 7 and therefore the opening pressure of the valve.

Figure 9:
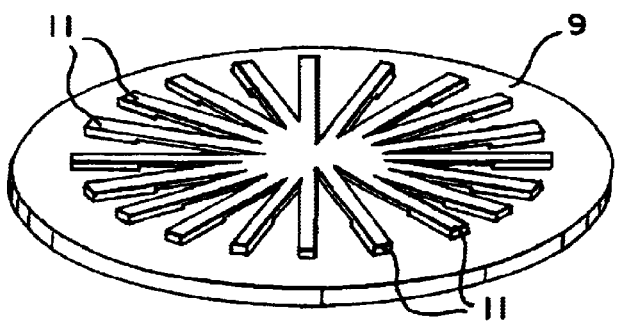
FIG. 9 is schematic perspective top view of a third embodiment of a micro valve according to the invention.
Figure 10:
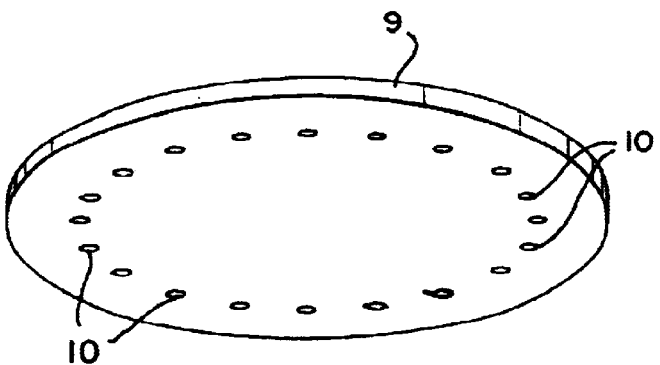
FIG. 10 is a perspective bottom view of the third embodiment depicted in FIG. 9.

With reference to FIGS. 9 and 10, a third embodiment of a valve according to the invention is disclosed. This embodiment provides a valve with an adjustable resistance to flow. A circular base plate 9 comprises, on its periphery, an array of openings 10 through which a fluid may flow. An array of actuating members 11 is arranged on the base plate 9 so that the free end of each actuating member 11 closes a corresponding opening 10 of the base plate. The SMA actuating members 11 are preferably extending from the center of the base plate 9 to the periphery of the plate.

In this embodiment, all the actuating members 11 have the same geometry but the geometry of the orifices 10 may differ in order to provide a range of different resistances to flow. A Peltier cell or an array of Peltier cells is integrated in the base plate 9, preferably in the center of the base plate so as to enable cooling of the complete array of SMA actuating members 11.

The setting or the actuating of the valve is similar to what has been disclosed in reference to the first embodiment at FIGS. 3 to 5.

Figure 11:
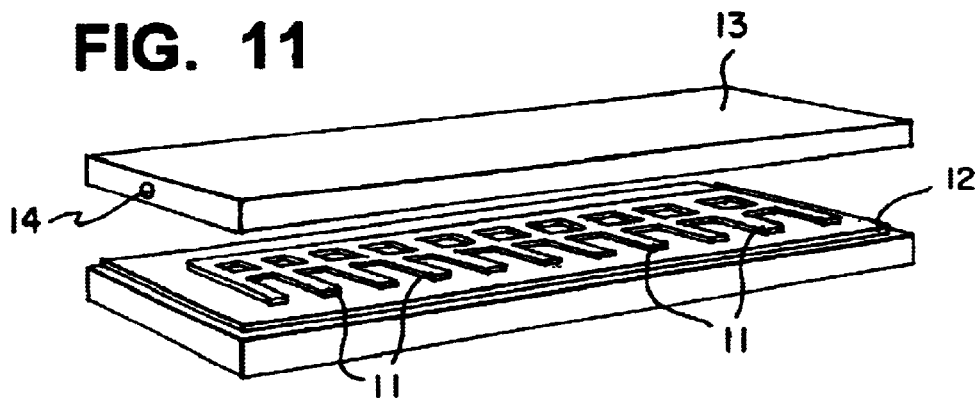
FIG. 11 is a perspective top view of an implantable assembly incorporating a valve according to the invention, the top cover being exploded.
Figure 12:
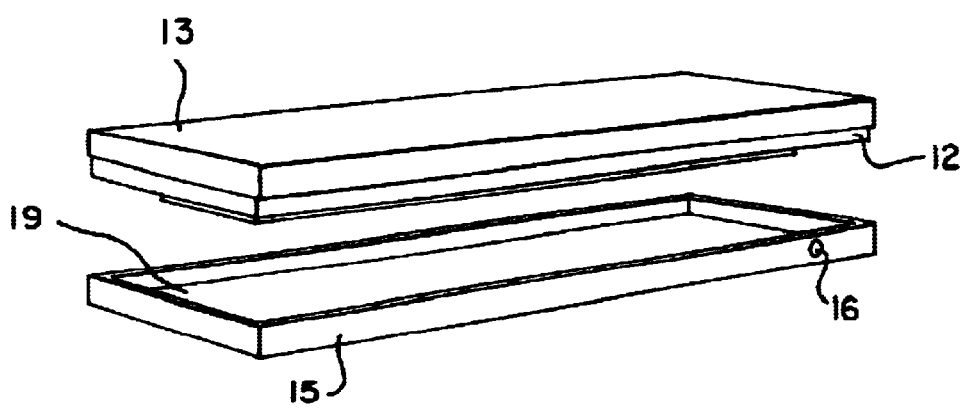
FIG. 12 is a perspective view of the assembly depicted in FIG. 11 with the bottom cover exploded.
Figure 13:
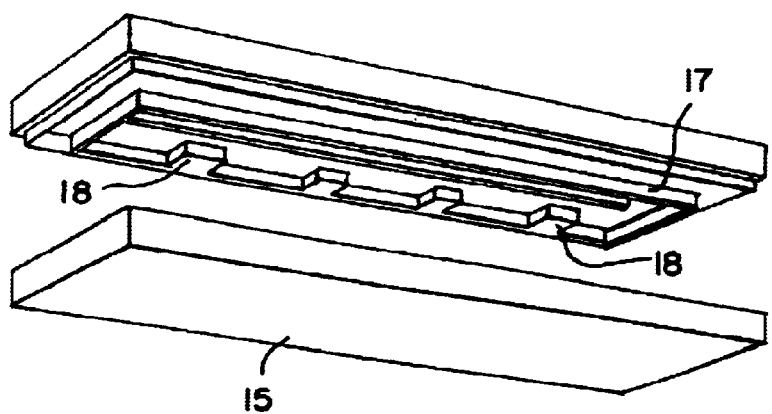
FIG. 13 is a bottom perspective view of the assembly shown at FIGS. 11 and 12.

FIGS. 11, 12 and 13 illustrate an implantable valve with adjustable opening pressure. The implantable valve comprises a valve assembly 12 according to one of the first or second embodiment disclosed above. A top cover 13 having a fluid outlet 14 is adapted to receive the valve assembly 12. An antenna 17 as well as the necessary electronic components 18 to power and control the valve assembly by telemetry are integrated on the bottom of the base plate of the valve assembly 12. A bottom cover 15 having a fluid inlet 16 and a leak tight compartment 19 for protecting the electronic components closes the structure.

The user may then power the assembly by telemetry and select non-invasively the opening pressure from outside the body by firstly cooling the SMA array of actuating members 11 and then selectively heating by Joule effect one or more actuating members 11. The electronic components 18 integrate a feedback mechanism that can be used to confirm that the correct actuating member 11 or array of actuating members have been heated.

A valve according to the invention may also be used in an implantable drug delivery pump. A few existing adjustable implantable pumps allow the user (patient and/or doctor) to select non-invasively a flow rate of chemicals to inject, due to an external programming unit. The existing devices can be divided in two main categories: the active or passive pumping mechanisms. In the first case, a battery energizes a pump that regulates the flow rate of chemicals. In the second case, a pressure reservoir "pushes" the chemicals out of the pump. The later concept is very elegant since the pumping does not require energy. Nevertheless, the regulation of the fluid flow is ensured by a valve, the opening of which depends on the power delivered to the valve. Therefore, a battery is still required.

Due to a valve according to the invention, when used in an implantable adjustable pump, the energy consumption problem is solved, since energy is only required to change the flow setting of the pump.

In the current products, energy is required continuously to keep the valve open. An adjustable passive pressurized pump embodying a valve according to the invention will now be disclosed with reference to FIG. 14.

The implantable pump comprises a pressurized reservoir 20 that contains the drug substance or other fluid to administrate. A valve assembly 21 as described with reference to the third embodiment shown in FIGS. 9 and 10 constitutes the adjustable flow resistance valve of the pump. The bottom of the base plate of the valve assembly 21 incorporates electronic components and an antenna that are used to power and control the valve non invasively by telemetry. A leak tight cover 22 protects the bottom face of the base plate and the electronics components, avoiding contact with the pressurized liquid contained in the reservoir 20. A top cover 23 having a fluid outlet 24 closes the structure.

The user may select the resistance of the valve from outside with a dedicated reading unit and therefore regulates the outflow of chemicals contained in the pressurized reservoir.

Many advantages are achieved with a valve according to the invention. Firstly, as the valve has multi stable states, energy is only required to switch from one state to the other. No energy is needed to maintain a selected state. Each state can either correspond to a selected opening pressure or to a flow resistance, depending on the application.

Second, the valve settings can be adjusted without a movement of any part. Only the elastic modulus of the material is modified and therefore the valve is less sensitive to blockage by clogs and other bio-substances.

The energy required is the energy needed to power a Peltier cell, and the energy for heating the actuating members. This energy can be provided to the implantable device by telemetry avoiding the use of batteries.

For medical applications, and more particularly for implantable adjustable valves or pumps as previously described, the choice of the SMA material is of importance. It must be chosen from the SMA materials that have two stable states at a temperature in the vicinity of the body temperature. Furthermore, the SMA material ideally should fulfill the following conditions. $M_s < T < A_s$ where T is the temperature of the human body and an hysteresis $\Delta T$, comprised between 10 and 40 degrees centigrade. TiNi (Nitinol) is a material that fulfills these requirements and which is also biocompatible.

It will be appreciated by persons skilled in the art that the present invention is not limited by what has been disclosed above, particularly with regards to the field of use of the valve, which may be integrated in other fluidic devices. Furthermore, the present invention may include combinations and sub-combinations of the various features disclosed as well as modifications and extensions thereof which fall under the scope of the following claims.

What is claimed is:

1. A method of setting and actuating an adjustable micro valve, the micro valve having a base element having a base plate face and at least two passages for the flow of fluid, at least one array of actuating members made of a SMA material arranged on the base plate face, the method comprising the steps of:

placing each of the actuating members adjacent to one of the at least two passages;

cooling the array of actuating members made of SMA material, to a temperature equal or below the temperature at which a transformation from austenitic to martensitic state occurs so that the entire array of SMA actuating members is either fully or partially in the martensitic state;

selecting at least one of the actuating members corresponding to a pre-determined opening pressure or resistance to flow; and heating individually each of the actuating members except the previously selected member to a temperature equal to or above the temperature at which a transformation from the martensitic state to the austenitic state occurs.

2. A method according to claim 1 wherein the actuating members are made of a SMA material having two stable states at body temperature and an hysteresis comprised between 10 and 40 degrees centigrade.

3. A method of setting and actuating an adjustable micro valve, the micro valve having a base element having a base plate face and at least two passages for the flow of fluid, at least one array of actuating members made of a SMA material arranged on the base plate face, the method comprising the steps of:

placing each of the actuating members adjacent to one of the at least two passages;

heating the array of actuating members made of SMA material, to a temperature equal or above the temperature at which a transformation from martensitic to austenitic state occurs so that the entire array of SMA actuating members is either fully or partially in the austenitic state;

selecting at least one of the actuating members corresponding to a pre-determined opening pressure or resistance to flow; and cooling individually the selected actuating members to a temperature equal or below to the temperature at which a transformation from the austenitic state to the martensitic state occurs.

4. A method according to claim 3 wherein the actuating members are made of a SMA material having two stable states at body temperature and an hysteresis comprised between 10 and 40 degrees centigrade.

* * * * *